United States Patent [19] [11] Patent Number: 4,737,461
Sugisawa et al. [45] Date of Patent: Apr. 12, 1988

[54] NOVEL BACTERIOLYTIC ENZYME AND PROCESS FOR PREPARING THE SAME

[75] Inventors: Ko Sugisawa, Nara; Masanori Yamamoto, Kaizuka; Osamu Fujii, Nishinomiya; Shinsuke Imai; Masayo Morino, both of Nara; Yoshiko Nishiwaki, Osaka, all of Japan

[73] Assignee: House Food Industrial Company Limited, Higashiosaka, Japan

[21] Appl. No.: 795,406

[22] Filed: Nov. 6, 1985

[30] Foreign Application Priority Data

Nov. 10, 1984 [JP] Japan .................. 59-237126

[51] Int. Cl.$^4$ .......... C12N 9/24; C12N 9/36; C12N 1/06; C12R 1/645
[52] U.S. Cl. .................. 435/200; 435/206; 435/259; 435/911
[58] Field of Search .............. 435/200, 206, 259

[56] References Cited

U.S. PATENT DOCUMENTS 3,963,577 6/1976 Shinkarenko et al. ......... 435/259 X
4,144,327 3/1979 Davies et al. ................. 424/94

FOREIGN PATENT DOCUMENTS 53-32189 3/1978 Japan .................. 435/259

OTHER PUBLICATIONS

O'Day in Chemical Abstracts vol. 80 (1974), p. 224, Abstract No. 130349h; and p. 188, Abstract No. 105751a.
ATCC Catalogue of Fungi/Yeasts, 16th edition, 1984, p. 250.

Primary Examiner—Lionel M. Shapiro
Attorney, Agent, or Firm—Oblon, Fisher, Spivak, McClelland & Maier

[57] ABSTRACT

A process for preparing a bacteriolytic enzyme comprising the steps of cultivating a Polysphondylium genus bacteria in a culture medium containing a carbon source, a nitrogen source, an inorganic salt and other nutritious ingredients, and then extracting an enzyme having a function of dissolving cell walls of microorganisms from the cultivated product.

6 Claims, 5 Drawing Sheets

NOVEL BACTERIOLYTIC ENZYME AND PROCESS FOR PREPARING THE SAME

BACKGROUND OF THE INVENTION

1. Field of the Invention

The present invention relates to a novel bacteriolytic enzyme and a process for preparing the same using a microorganism of cellular slime mold of Polysphondylium genus.

2. Description of the Related Art

The known methods for rupturing the cell walls may be divided into the three main categories of (1) physical methods, (2) chemical methods and (3) enzymatic methods. The physical and chemical methods involve unavoidable problems concerning the processing systems, and the products are apt to be changed by excessive processing. Enzymatic methods or processes have accordingly been attracting more public attention in recent years.

Enzymes for dissolving germ bodies used for this purpose are generally referred to as bacteriolytic enzymes, and the most popular such enzyme is lysozyme prepared from albumen. However, the bacteriolytic spectrum of the albumen lysozyme only covers some gram-positive bacteria, and the albumen lysozyme has the disadvantage of not acting on general lactic acid bacteria such as typified by the Lactobacillus and Streptococcus genera.

Japanese Patent Publication No. 8597/1982 discloses a method wherein an enzyme composition (containing cellulase, laminarinase, xylanase, pectinase, amylase, protease, etc.) produced by a microorganism of Illupec(?), Coryollus(?) or Coprynus(?) genus of Basidiomycetes is allowed to act on a cell membrane (chlorella membrane) to rupture the membrane. However, this prior art Publication does not refer to any microorganism of Polysphondylium genus.

The growth of a Polysphondylium genus microorganism of cellular slime mold in a simple nutrient medium has been reported in Science, Vol. 139, page 338 (1963). However, no enzyme was extracted from the culture medium after cultivation.

After a vigorous search for a novel enzyme having a bacteriolytic spectrum which is wider than that of albumen lysozyme, we have succeeded in separating a cellular slime mold, more specifically a novel microorganism (novel germ specie) of Polysphondylium, which exhibits a rapid bacteriolytic function on the lactic acid bacteria which have not been attacked by the albumen lysozyme. The present invention is accomplished on the basis of the aforementioned finding.

SUMMARY OF THE INVENTION

The enzyme of the invention is prepared from an extraordinary source in that it is prepared by the cultivation of a cellular slime mold, as described above. Moreover, it has an advantageous feature that the bacteriolytic spectrum thereof is wider than that of the known albumen lysozyme. The enzyme of the invention is a novel bacteriolytic enzyme which is active in a lower acidic region wherein the conventionally known bacteriolytic enzymes, for example prepared from *Achromobacter lunatus* and *Bacillus subtilis*, are not active.

DESCRIPTION OF THE INVENTION

Figure 1:
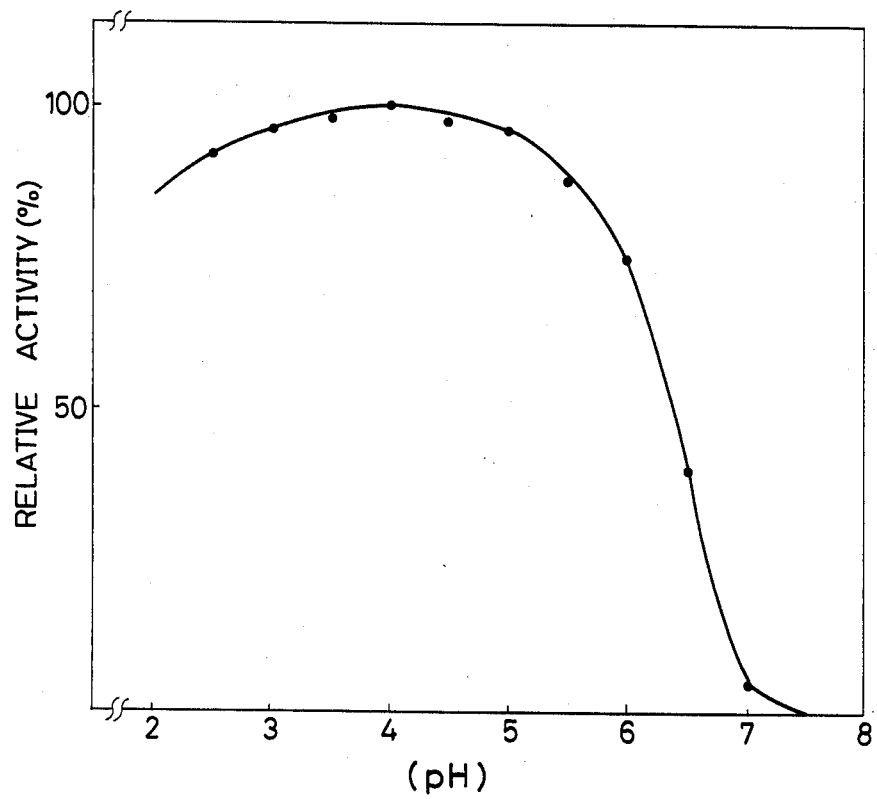
FIG. 1 is a graph showing the optimum pH curve of the enzyme prepared by the present invention.

We have separated a number of microorganism species from the soils of various places, and investigated the products thereof to check whether they have a bacteriolytic enzyme. As a result of our investigation, we have succeeded in separating novel bacteria which produce the enzyme having the aforementioned characteristics.

The thus separated microorganism species are designated Polysphondylium Pallidum LE-1 (Deposited with the Fermentation Research Institute, Agency of Industrial Science and Technology, Bikoken FERM BP-633) and *Polysphondylium violaceum* LE-1 (Deposited with the Fermentation Research Institute, Agency of Industrial Science and Technology, Bikoken FERM BP-632). They have been identified as cellular slime molds of Polysphondylium genus by the method described by Lindsay S. Olive in "The Mycetozoans" (1975).

The microbiological characteristics of the molds are as follows:

(1) Sorocarps with a broader stalk tube that is filled with a framework of empty cells, this being the characteristic feature of Dicryosteliaceae.

(2) Sorocarps with large terminal sorus and regular whorls of smaller stalked sori along the main stalk, this being the characteristic feature of the Polysphondylium.

(3-i) Sorocarps with large terminal sorus and regular whorls of smaller stalked sori along the main stalk and is colored with reddish purple, this being the characteristic feature of the *Polysphondylium violaceum*.

(3-ii) Sorocarps with large terminal sorus and regular whorls of smaller stalked sori along the main stalk and is colored with white, this being the characteristic feature of the *Polysphondylium pallidum*.

The process of the invention comprises the step of inoculating and cultivating a mold which belongs to the Polysphondylium genus and produces a bacteriolytic enzyme in a culture medium.

Any solid or liquid media may be used for this purpose. It is generally convenient to use a liquid culture medium and to effect cultivation in an aerobic atmosphere, for example, cultivating under shaking or cultivating under aeration and agitation.

An ordinary culture medium may be used as the culture composition. Saccharides, such as glucose and lactose, may be used as the carbon source, and organic and inorganic nitrogen-containing compounds, such as peptone, enzyme extracts, dried bacteria bodies, skimmed milk, ammonium salts and nitrates, may be used as the nitrogen source. Phosphates or sulfates of metallic elements, such as potassium and magnesium, may be added as the inorganic salt.

The condition for cultivation may be selected or adjusted so that the maximum quantity of the produced bacteriolytic enzyme is accumulated. We have found that a satisfactory result may be obtained by setting the pH value of the culture medium to pH 4.0 to 8.0, preferably pH 5.5 to 7.0, and by cultivating at a temperature of from 15° to 40° C., preferably from 20° to 30° C., for 2 to 4 days.

The desired bacteriolytic enzyme is thus accumulated in the cultivation solution and the cultivated mold body.

In the present invention, the desired enzyme may be extracted through ordinary separation and refining means. Enzyme products having any desired purity may be prepared.

More specifically, the enzyme may be separated in the following manner.

Initially, the cultivated mold body is separated from the cultivation solution by means of centrifugal separation or filtration. The separated mold body is crushed by means of ultrasonic waves or other means, and the residue of cells is removed by centrifugal separation to obtain a supernatant solution. This supernatant solution may be used directly without any further processing. Alternatively, the supernatant solution may be processed similarly to the cultivation solution to obtain the desired product, as will be described in detail hereinafter.

The cultivation solution is directly subjected to salting-out by the addition of a salt, such as ammonium sulfate, or the addition of a hydrophilic organic solvent, such as alcohol and acetone, to fractionate and precipitate the desired product.

The refining degree may be further increased by a method wherein the product is absorbed by and then removed from an ion exchange resin, or by a gel filtration method wherein Sephacryl (Trade Name, produced and sold by Pharmacia Fine Chemicals) or Toyopearl (Trade Name, produced and sold by Toyo Soda Manufacturing Co., Ltd.) is used. These methods may be used singly or in combination.

The enzyme of the invention is active in a wide pH range of from about 2 to 7. It has a particularly high activity within an acidic range of pH 3 to 6. (In this connection, reference should be made to FIG. 1. In the experiment, the pH value is adjusted using a McIlvaine buffer solution having an ionic strength of 0.06.)

Figure 2:
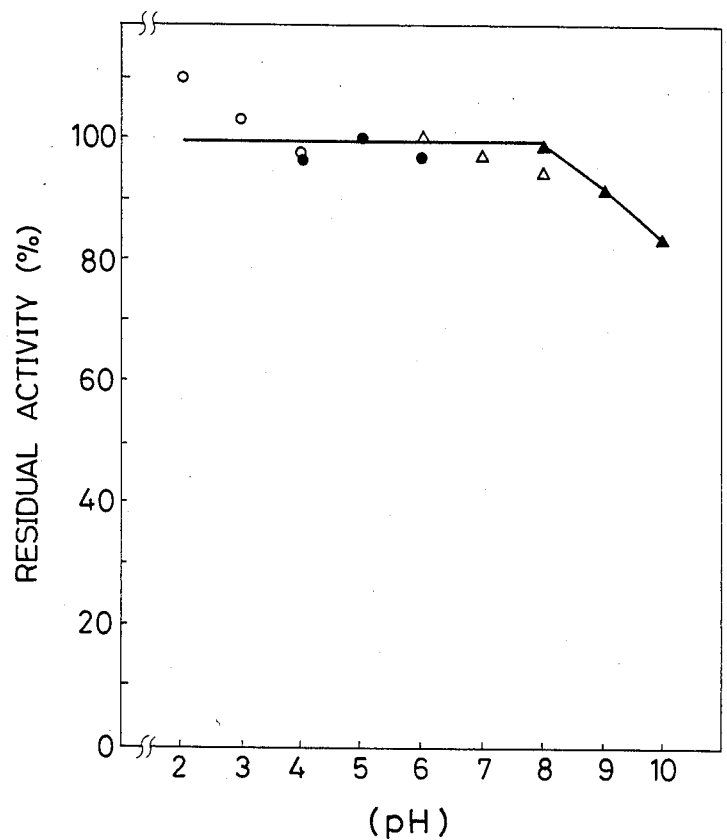
FIG. 2 is graph showing the stability of the enzyme prepared by the present invention.

The enzyme is relatively stable within the pH range of about 2 to 8. (In this connection, reference should be made to FIG. 2 showing the stability of the enzyme with the change in pH value. The graph in the FIGURE was obtained by plotting the activities of the residual enzyme after the enzyme prepared by the process of the invention had been maintained at the plotted pH values at 30° C. for 16 hours. The buffer solutions used for the adjustment of pH value are as follows:

pH 2 to 6 (denoted by ◯): Glycin/Hydrochloric Acid Buffer Solution (0.01 M)
pH 4 to 6 (denoted by ●): Acetic Acid Buffer Solution (0.01 M)
pH 5 to 8 (denoted by △): Phosphoric Acid Buffer Solution (0.01 M)
pH 8 to 10 (denoted by ▲): Ammonium Buffer Solution (0.01 M)

Figure 3:
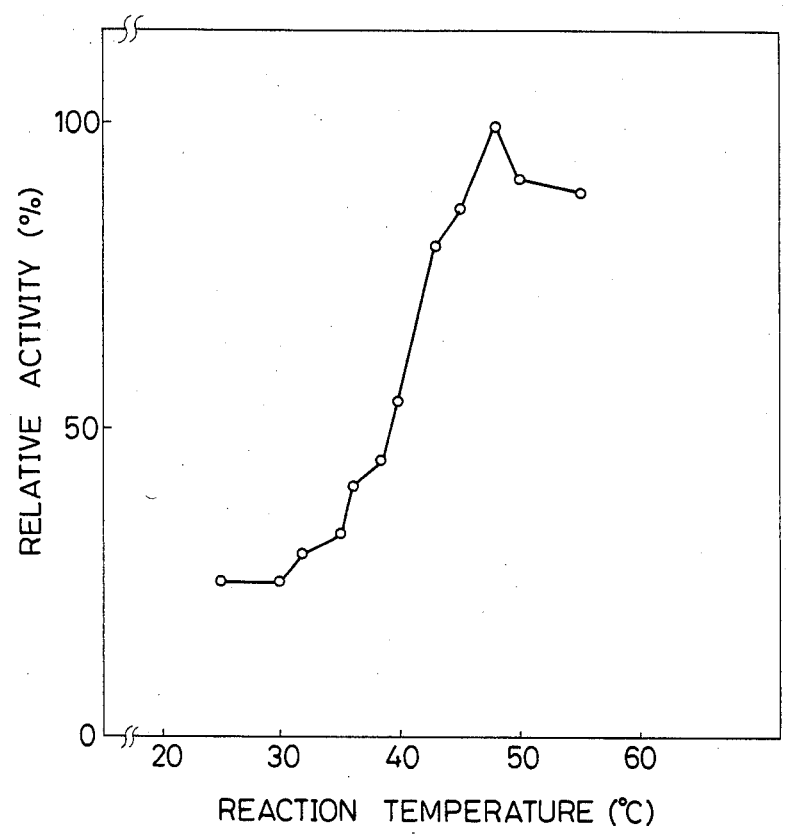
FIG. 3 is a graph showing the optimum temperature for the enzyme prepared by the present invention.

The optimum temperature for the enzymatic reaction is about 45° to 55° C. (See FIG. 3.)

Figure 4:
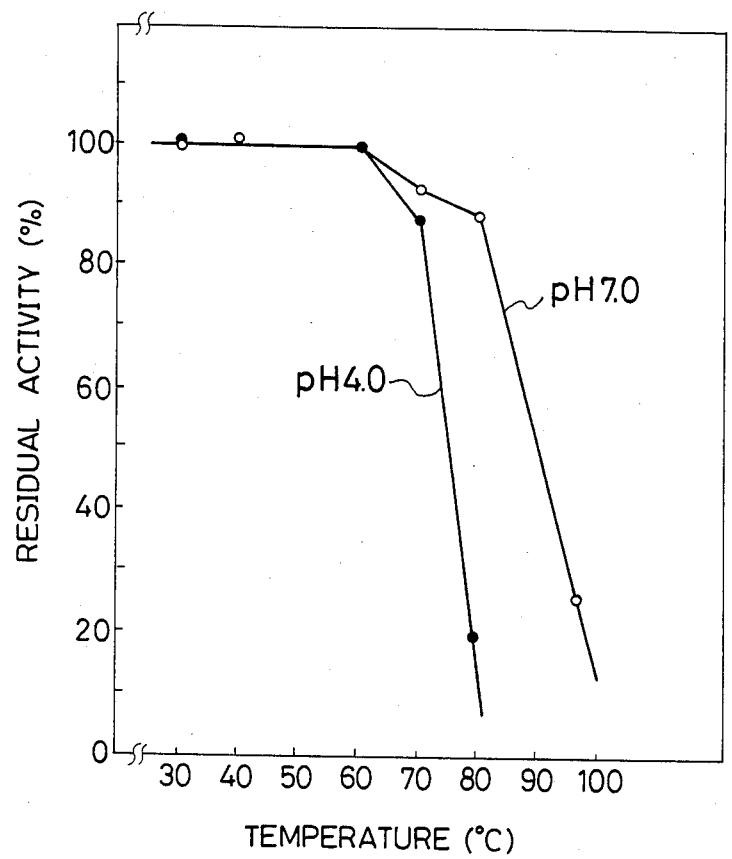
FIG. 4 is a graph showing the thermal stability of the enzyme prepared by the present invention.

The enzyme has a sufficient thermal stability in that it is stable even after being heated at 60° C. for 15 minutes. (In this connection, reference should be made to FIG. 4 showing the results of an experiment for the confirmation of thermal stability. In the experiment, the enzyme was added, respectively, to a 0.01 M acetic acid buffer solution having a pH value of 4.0 and a 0.01 M phosphoric acid buffer solution having a pH value of 7.0, and then heated at the plotted temperatures, and the residual activity of the enzyme was measured.)

The dissolution function of the enzyme was measured or calculated in the following manner.

Unless otherwise specified, the used substrate was a dried bacterium body (produced by Sigma Chemical Company) of *Microccus lysodeikticus*. The substrate was added to a McIlvaine buffer solution (pH 3.5, ionic strength, 0.06) to prepare a suspension. 0.1 ml of the enzyme solution was added, to 3.0 ml of the suspension having an optical density (hereinafter referred to simply as O.D.) at 570 mµ of 0.7, and the suspension was maintained at 37° C. The bacteriolytic activity was identified by the decrease in turbidity at the aforementioned wave length. The quantity of the enzyme required for decreasing the O.D. at 570 mµ by 0.001 per minute was defined as one unit of bacteriolytic activity. A suspension having water added in place of the enzyme solution was used as the control.

Figure 5:
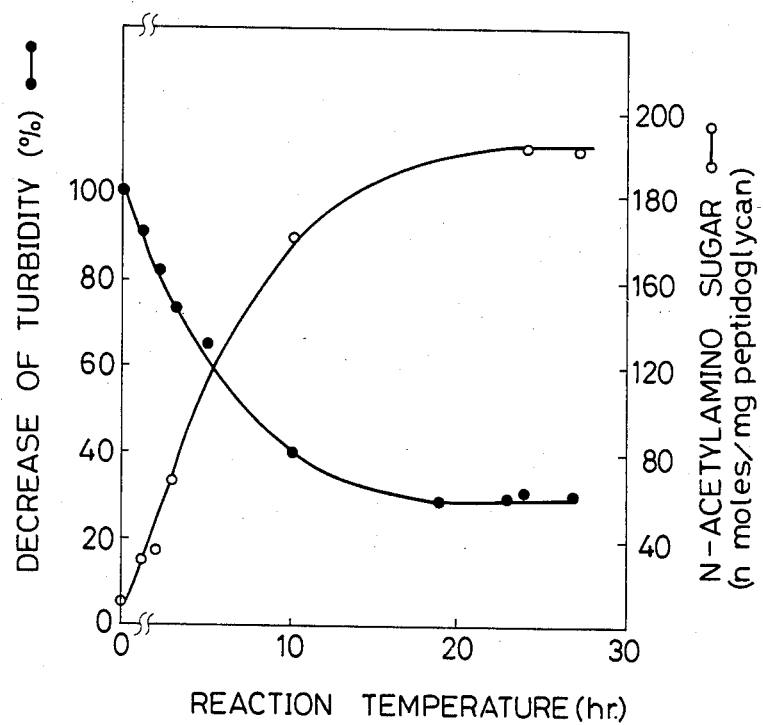
FIG. 5 is a graph showing the solubilization capacity of the enzyme prepared by the present invention.

The novel bacteriolytic enzyme composition of the invention was subjected to ion exchange chromatography, revealing that at least three active components for dissolving the Microccus Lysodeikticus were included. It is understood from the result that the composition is a mixture of a few enzymes. In extraction and refining of the enzyme composition, individual enzymes may be refined and isolated completely for a partially refined mixture including three or more enzymes of desired purity may be extracted for use. As shown in FIG. 5, as the dissolution proceeds, hexosamine is solubilized. Hexosamine is colored by the Morgan-Elson reaction.

The curves in FIG. 5 were obtained in the following manner.

To 7.5 ml of the enzyme solution dissolved in a 0.01 M acetic acid buffer solution was added 15 mg of peptidoglycan of *B. megaterium* to react at 37° C. The decrease in turbidity was represented by the change of O.D. at 570 ml. The N-acetylamino sugar was quantitatively analysed in accordance with the method of Ghysen et al. (Elizabeth F. Neufeld et al., Methods in Enzymology "Complex Carbohydrates", vol. VIII, pp 691–692, 1966).

The bacteriolytic enzyme composition prepared by the present invention has a bacteriolytic spectrum which is considerably wider than that of the albumen lysozyme. In other words, it exhibits the bacteriolytic function on almost all gram-positive bacteria including lactic acid bacteria. A particularly remarkable characteristic is that it is active in a low acidic range within which the known bacteriolytic enzymes have relatively poor activities.

The enzyme composition of the invention may be used as an antibiotic in the medical and pharmaceutical fields. It may be also used as a natural antiseptic producing little adverse reaction in the field of foodstuff production. It is expected that the enzyme composition of the invention may be used for wide a range of applications, including cell fusing, which in recent years has become an active topic in biotechnology.

EXAMPLE 1

Into a 50 l volume cultivation tank, was placed 15 of a liquid culture medium containing 0.5% of peptone, 0.05% of a yeast extract, 0.5% of glucose, 0.225% of potassium phosphate, 0.067% of dipotassium hydrogenphosphate and 0.05% of magnesium sulfate (heptahydrate), and the contents of the tank were sterilized by heating at 121° C. for 15 minutes. After inoculation with Klebsiella aerogenes, cultivation was continued for 48 hours at 35° C. and 150 rpm under an aeration rate of 20 l/min. The bubbles generated by the growth of the germ was prevented by the addition of a defoaming agent. After the completion of cultivation, the culture solution was sterilized at 121° C. for 5 minutes, and a *Polysphondylium pallidum* LE-1 amoeba which had been cultivated in a vibrating flask for two days was added to the sterilized culture solution, followed by cultivation at 25° C. and 150 rpm under an aeration rate of 20 l/min. After the completion of cultivation, the cultivation solution was subjected to centrifugal separation to separate the amoeba cells (97 g wet weight) which were rinsed with deionized water and to which was then added water of a quantity 50% by weight of the cells. The admixture was put into an ultrasonic oscillator to break or crush the cells at 20 KHz for 20 minutes. The residue of cells was removed by centrifugal separation to obtain 110 m of a supernatant solution. The enzymatic activity of the supernatant solution was 180 units/1 ml.

EXAMPLE 2

684 g of ammonium sulfate (septahydrate) was added to 1000 ml of the supernatant solution cultivated similarly as in Example 1 and deprived of the amoeba cells, and the admixture was allowed to stand at 4° C. for one night to salt out the precipitate which was collected by centrifugal separation. The collected precipitate was dialyzed with a sufficient amount of water which was concentrated to obtain 50 ml of dialysis liquid. The enzymatic activity of the thus concentrated dialysis liquid was 55 units/1 ml.

EXAMPLE 3

The supernatant solution prepared in Example 1 was used as an enzyme source to conduct dissolution experiments to learn the dissolution activity thereof on various microorganism bodies. The germs as set forth in Table 1 were cultivated in liquids, followed by collection of germ bodies through centrifugal separation, and the germ bodies were suspended in a McIlvanine buffer solution (pH 3.5, Ionic Strength: 0.06). The bacteriolytic activities on respective germs were determined by the determination method as described hereinbefore.

The results are shown in Table 1.

In determination of the bacteriolytic activities of lysozyme, a phosphoric acid buffer solution (pH 7.0, ionic strength, 0.06) was used in place of the McIlvaine buffer solution and a lysozyme solution (concentration: 15 μg/mg) was used in place of the enzyme composition of the invention, the other procedures being the same.

As will be apparent from Table 1, the enzymes of the invention act on a wider veriety of germs under an acidic condition of pH 3.5 than those attacked by the albumen lysozyme.

TABLE 1

| Germ Specie | Albumen Lysozyme (Control) | Enzyme of the Invention |
|---|---|---|
| Lactobacillus arabinosus | − | +++++ |
| Lactobacillus bulgaricus | + | +++++ |

TABLE 1-continued

| Germ Specie | Albumen Lysozyme (Control) | Enzyme of the Invention |
|---|---|---|
| Lactobacillus casei | + | ++ |
| Streptococcus faecalis | (+) | +++ |
| Streptococcus thermophilis | − | +++++ |
| Streptococcus lactis | − | +++++ |
| Bacillus subtilis | +++ | +++ |
| Bacillus megaterium | ++++ | +++++ |
| Bacillus licheniformis | + | +++ |
| Bacillus polymyxa | − | +++++ |
| Bacillus cereus | − | − |
| Micrococcus lysodeikticus | +++++ | +++++ |
| Staphylococcus epidermidis | − | − |
| Arthrococcus simplex | (+) | +++++ |
| Brevibacterium ammoniagenes | − | (+) |
| Corynebacterium fascians | − | − |
| Escherichia Coli | − | − |
| Alcaligenes faecalis | − | (+) |
| Enterobacter aerogenes | − | − |

Note:
The decrease of O.D. at 570 mμ (%) is identified by the following:
0 to less than 8: −
8 to less than 10: (+)
10 to less than 20: +
20 to less than 40: ++
40 to less than 60: +++
60 to less than 80: ++++
Not less than 80: +++++

EXAMPLE 4

Each of ten 500 ml Sakaguchi flasks was charged with 50 ml of a liquid culture medium containing 0.5% of peptone, 0.05% of a yeast extract, 0.5% of glucose, 1.0% of a freeze-dry bacterium body of Klebsiella aerogenes, 0.225% of potassium dihydrogenphosphate, 0.067% of dipotassium hydrogenphosphate and 0.05% of magnesium sulfate (heptahydrate), and sterilized at 121° C. for 15 minutes. Then, the amoeba of Polysphondylium Pallidum LE-1 was inoculated into each flask, followed by vibrating cultivation at 22° C. for 3 days. After the completion of cultivation, the cells of the amoeba were broken and the supernatant solution was separated by centrifugal separation. The enzymatic activity of the supernatant solution was measured to find that the activity per 1 ml of the solution, which was 170 units. The supernatant solution was subjected to salting-out with ammonium sulfate followed by subsequent dialysis, and the enzymatic activity of the dialyzed solution was measured and found to be 46 units.

EXAMPLE 5

Each of ten 500 ml Sakaguchi flasks was charged with 50 ml of a liquid culture medium containing 0.08% of soybean lecitine, 2% of skim milk, 1% of proteose peptone and 0.68% of potassium dihydrogenphosphate, and sterilized at 121° C. for 15 minutes. Then, the amoeba of *Polysphondylium pallidum* LE-1 was inoculated into each flask, followed by vibrating cultivation at 22° C. for 3 days. After the completion of cultivation, the cells of the amoeba were separated from the culture medium solution by centrifugal separation. The enzymatic activity of the supernatant solution separated from the broken amoeba cells was measured similarly as in Example 2 and found to be 72 units per 1 ml of the solution. The supernatant solution of the cultivated medium was subjected to salting-out with ammonium sulfate followed by subsequent dialysis, similarly as in Example 2, and the enzymatic activity of 50 ml of the dialyzed solution was measured and found to be 60 units/1 ml.

EXAMPLE 6

The amoeba of Polysphondrylium violaceum LE-1 was cultivated under vibration for 3 days under the same condition as described in Example 4. After the completion of cultivation, the amoeba cells were collected by centrifugal separation and the cells were broken by ultrasonic waves similarly as in Example 1. The enzymatic activity of the supernatant solution separated through centrifugal separation was 170 units/1 ml and effective on a variety of microorganisms referred to in Example 3, showing bacteriolytic functions thereon. To 100 ml of the supernatant solution of the culture medium separated from the amoeba cells was added ammonium sulfate for salting-out, and the precipitate was dissolved in a small amount of water and then subjected to dialysis to obtain 50 ml of a concentrated enzyme solution. The enzymatic activity of the thus concentrated solution was 42 units/1 ml.

What is claimed is:

1. A process for preparing a bacteriolytic enzyme comprising the steps of cultivating a *Polysphondylium pallidum* LE-1 (Bikoken FERM BP-633) or *Polysphondylium violaceum* LE-1 (Bikoken FERM BP-632) bacterium in a culture medium containing a carbon source, a nitrogen source, an inorganic salt and other nutritious ingredients, and then extracting said bacteriolytic enzyme from the cultivated product.

2. The process according to claim 1, wherein said carbon source is glucose or lactose.

3. The process according to claim 1, wherein said nitrogen source is at least one selected from the group consisting of dried germ bodies and skimmed milk.

4. The process according to claim 1, wherein said inorganic salt is phsophate or sulfate of potassium or magnesium.

5. The process according to claim 1, wherein cultivation is effected at a pH of from 4.0 to 8.0 and at a temperature of from 15° to 40° C. for 2 to 4 days.

6. A bacteriolytic enzyme obtained from *Polysphondylium pallidum* LE-1 (Bikoken FERM BP-633) or *Polysphondylium violaceum* LE-1 (Bikoken FERM BP-632) having a high activity within an acidic range of pH 3 to 6, being stable at a pH range of from 2 to 8, having an optimum activity at a temperature of from 45° to 55° C., being stably sustainable to heating at 60° C. for 15 minutes, having a bacteriolytic activity to Microccus Lysodeikticus, and having a bacteriolytic spectrum which is wider than that of albumen lysozyme.

* * * * *